US007193101B2

(12) United States Patent
Daly

(10) Patent No.: US 7,193,101 B2
(45) Date of Patent: *Mar. 20, 2007

(54) ESTERS WITH ANTIMICROBIAL, BIORESISTANT AND FUNGAL RESISTANT PROPERTIES

(75) Inventor: Thomas Daly, Chicago, IL (US)

(73) Assignee: TPAT IP, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 11/209,377

(22) Filed: Aug. 23, 2005

(65) Prior Publication Data

US 2005/0287094 A1    Dec. 29, 2005

Related U.S. Application Data

(60) Provisional application No. 60/603,719, filed on Aug. 23, 2004.

(51) Int. Cl.
*C07C 255/00* (2006.01)
*C07C 205/00* (2006.01)
*A61K 8/00* (2006.01)

(52) U.S. Cl. .............. 558/441; 558/442; 560/156; 560/158; 424/63

(58) Field of Classification Search .............. None
See application file for complete search history.

(56) References Cited

U.S. PATENT DOCUMENTS 5,109,020 A * 4/1992 Negele et al. .............. 514/519

FOREIGN PATENT DOCUMENTS

JP    2000053502 A2 *  2/2000

OTHER PUBLICATIONS

Mdoe et al. Catalysis of the Michael reactions by N, N'-dimethylaminopropyl derivatised micelle templated silica: effects of solvent and loading. Bulletin of the Chemical Society of Ethiopia, 2003, vol. 17 (2), p. 219-233, ACS document No. 141:71146.*
Park et al. Viologen-mediated reductive transformations of gem-bromonitro compounds and alpha-nitroketones by sodium dithionite. Bulletin of the Korean Chemical Society, 1993, vol. 14 (4) p. 461-465, ACS documents No. 120:133483.*
Takeuchi et al. The First General and Efficient Method for the Synthesis of Tetriary Alkyl Fluorides. Journal of Organic Chemistry, 1993, vol. 58 (13) p. 3483-3485.*
Piquet et al. Michael Additions of Carbonucleophiles to Butenone Catalyzed by the Non-Hydride [Ru(O2CH)(CO)2(PPh3)]2 Complex. Tetrahedron, 1999, vol. 55 (13) p. 3937-3948.*
Klemm et al. Thin-layer chromatagraphic studies on derivatives of the biocide 2-bromo-2-nitropropane. Journal of Chromatagraphy, 1988, vol. 438 (1), p. 122-125. See ACS doc. No. 109:21609.*

* cited by examiner

*Primary Examiner*—Sikarl A. Witherspoon
(74) *Attorney, Agent, or Firm*—Clifford Kraft

(57) ABSTRACT

A bromine/nitro moiety linked into the backbone of an ester or other compound over a wide range of occurrence rates provides antimicrobial, bio-resistant and fungal resistant properties for metal working fluids (MWF)s, coatings, plastics, and medical devices. The moiety can be have the bromo and nitro groups linked to the same or different carbon atoms. The present invention also relates to urethanes, urea, amides, imides, carbonates, ethers, siloxanes, and many other types of linkages essential to MWF bases.

4 Claims, 4 Drawing Sheets

ESTERS WITH ANTIMICROBIAL, BIORESISTANT AND FUNGAL RESISTANT PROPERTIES

This application is related to and claims priority from United States Provisional Patent application number 60/603,719 filed on Aug. 23, 2004, copending application number 10/603,356 filed Jun. 25, 2003 and copending application number 11/193,776 filed Jul. 29, 2005.

BACKGROUND

1. Field of the Invention

The present invention relates to the field of esters and more particularly to esters with bioresistant, fungal resistant and antimicrobial/antifungal properties.

2. Description of the Problem Solved by the Invention

Due to environmental regulation, the use of tin, mercury, lead, and other heavy metals to control the growth of microbes in organic systems is now prohibited. In particular metal working fluids (MWF)and metal working fluid bases suffer a failure mode when attacked by microbes. The problem is especially acute in water extendable and emulsion MWF systems. The attack of the microbes on the MWF base causes the pH of the system to drop, which destabilizes the emulsion and also increases the corrosion of metal parts that are exposed to the attacked fluid. Aside from the obvious problems that microbes cause in MWFs, operator health issues also arise due to continuous exposure to high levels of bacteria. Current systems in place such as pigment dispersants and MWFs include the addition of biocides to the fluid to prevent the bacteria from breaking down the MWF. One common biocide in use is the family of isothiazolinones. This product is generally hazardous to handle and causes sensitization in many people when exposed repeatedly. The sensitization often takes the form of itching all over the body, or hives when any part is in contact with the isothiazolinone. Additionally, the isothiazolinone family is relatively unstable at the alkaline pH that most MWFs are maintained at. This then requires the operator to add more material on a regular basis. Also, the microbes develop a tolerance to isothiazolinones. This again requires the operator to increase the amount of the isothiazolinone in the system.

A second biocide technology is the use of formaldehyde condensates. These materials are generally hazardous, but do not lead to sensitization of the operators in contact with the MWF. The formaldehyde condensates do contribute to free formaldehyde in the workplace, but the results are not consistent as to how much formaldehyde they contribute to the workplace atmosphere. Most formaldehyde condensates are volatile and evaporate. This requires their replenishment on a regular basis even when they are not consumed.

What is needed is a system that uses an ester as the MWF base that is not susceptible to microbial attack. The material fails to act as a food source for the microbes that are able to digest the current MWF bases.

SUMMARY OF THE INVENTION

The present invention relates to an ester for use in a pigment dispersant or MWF that contains an antimicrobial moiety that is linked into the backbone of the molecule. This moiety is, in general, a bromine atom and a nitro (NO2) group linked to one or more of the carbon atoms forming the backbone of the molecule that is the pigment dispersant or MWF base. While the present invention is directed primarily to esters, the moiety taught should also be effective when linked onto a carbon atom in the backbone of any suitable pigment dispersant or MWF base molecule. The moiety can appear in the backbone of the base in various levels of occurrence. A preferred occurrence of around 1000 parts per million on a weight basis is effective; however the frequency of occurrence can be as low as 5 parts per million to as high as 99–100%. Pigment dispersant and MWF base types within the scope of the invention include, but are not limited to urethane, urea, amide, ester, carbonate, ether, and siloxane linkages.

It is well known in the art to combine a carboxylic acid and an alcohol in the presence of a suitable catalyst to form an ester. The present invention adds a bromo-nitro substituted alcohol, diol or polyol to a standard alcohol to be used in the ester synthesis. The proportion of substituted compound used is chosen to yield the desired concentration of the moiety in the final MWF base. A preferred diol for the application is bromonitropropanediol or 2-bromo-2-nitro-propane-1-3-diol or simply BNPD. This particular diol is a solid material with varying degrees of solubility in other alcohols and has proven antimicrobial properties.

In addition, BNPD has been shown to have no tetragenecy (cancer causing effects) and is approved by the CFTA at levels of up to 0.1% for use in cosmetics. BNPD has also been used in baby wipes for its antimicrobial properties.

The fact that the active antimicrobial moiety is covalently linked directly into the backbone of the ester reduces its breakdown at the alkaline pHs required of MWFS. In addition, the moiety is not photo-active or decomposed by sunlight or exposure to mineral salts such as calcium chloride, magnesium hydroxide and sodium chloride as are found in hard and softened water.

Because BNPD is a substituted diol, it is a natural reactant to form part of an ester linkage with a carboxylic acid. Also, being a diol, it mixes directly with a wide range of alcohols or polyols and other performance enhancing additives with no difficulty or adverse reactions. In fact, it can be mixed in any desired proportion (to the extent that it is soluble) with any standard alcohol used in synthesizing esters, ethers, or urethane type linkages.

While bromonitropropanediol (BNPD) is the preferred antimicrobial agent because of its proven activity and its benign effects on the environment and on humans, other alcohols, diols or polyols with bromine and nitro groups linked at the same or different carbon atoms can also be incorporated into the backbone of MWF bases. Any other antimicrobial agents that can be linked onto an alcohol reacted linkage are within the scope of the present invention.

DETAILED DESCRIPTION OF THE INVENTION

Figure 1:
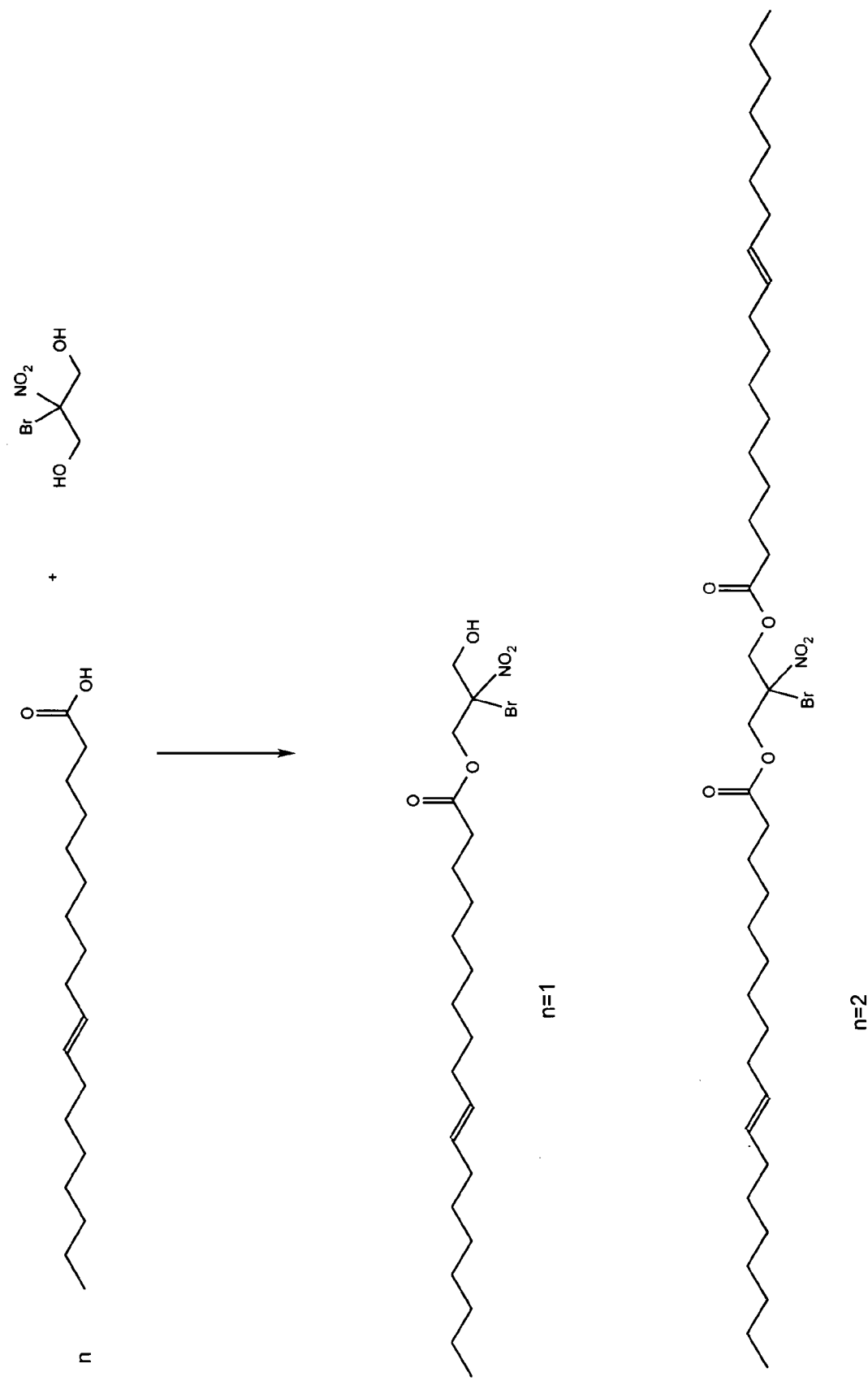
FIG. 1 shows the formation of an ester linkage with BNPD.

It is well known in the art to combine alcohols with carboxylic acids to form ester linkages. One example is isopropyl oleate, the ester of isopropyl alcohol and oleic acid. Polyols are also commonly used, such as in the production of Lexolube 21–214 by Innolex. A typical ester will have the following formula:

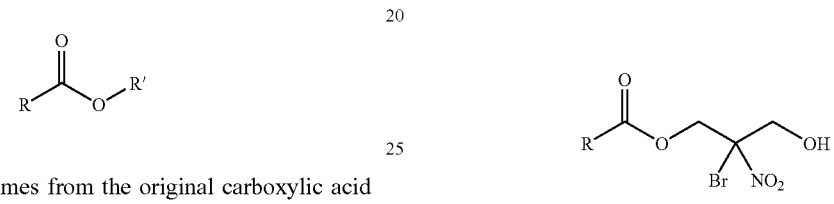

where R typically comes from the original carboxylic acid and R' typically comes from the original alcohol. It is well known in the art that R and R' can be the same or different. The typical example noted above as isopropyl oleate has the following structure:

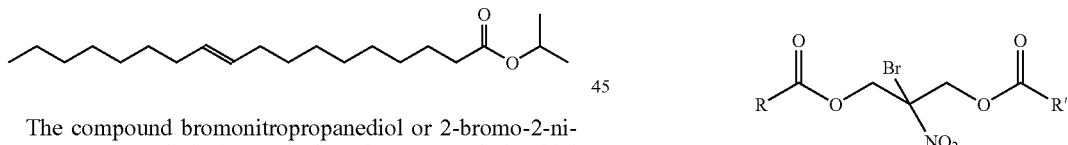

The compound bromonitropropanediol or 2-bromo-2-nitro-propane-1,3-diol (BNPD) has known antimicrobial properties. Tests on this compound have shown that it is effective against various strains of both gram positive and gram negative bacteria in concentrations of 1–50 ppm with the average minimum inhibitory concentration being around 25 ppm. In addition, work has indicated that BNPD is also antifungal. BNPD has the following structure:

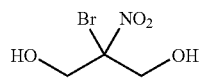

Because BNPD is a polyol, it can be combined with other alcohols, diols, or polyols in the manufacture of the esters used as MWF bases. In particular, BNPD alone or mixed with other alcohols, can be combined with carboxylic acids to form esters that are suitable for use as MWF bases. This causes the active moiety to become covalently linked into the ester. In the case of the oleate ester, the product is:

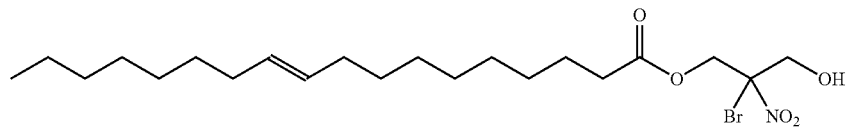

Or more generally:

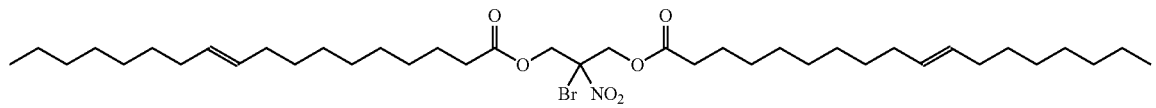

The dioleate ester can easily be made, which has the following structure:

Or more generally, for the diester:

While BNPD is a preferred polyol starting point to link the active moiety into an ester MWF base, it is within the scope of the present invention to use many other materials that contain a bromine atom and nitro group linked near one another. The preferred class of compounds contains the bromine and nitro linked to the same carbon atom; however, it is felt that a moiety where the bromine and nitro are not linked to the same carbon, but near each other will still be effective. Many other similar compounds can also be used. In particular, bromonitromethanediol, bromonitroethanediol, bromonitrobutanediol, etc. can also be substituted into molecule backbones with similar results. It should be understood that these are just examples of the many compounds within the scope of the present invention. The prior art has shown that bromonitromethane is effective for the treatment of nematodes in the soil (See U.S. Pat. No. 5,013,762 which is hereby incorporated by reference) and as a general biocide (See U.S. Pat. No. 5,866,511 which is hereby incorporated by reference). It is felt that bromonitromethanediol and similar diols are equally effective.

The present invention also includes using a BNPD or BNPD analog as the terminus, such as:

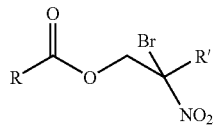

Where R' can be, but is not limited, to CH2OH, OH, CH3, or H.

The present invention reacts BNPD or similar substituted alcohols, diols or polyols, with or without the aid of a solvent or co-solvent, with a carboxylic acid to form the ester MWF base.

The present invention results in a covalently linked bromine/nitro moiety in the backbone of an ester at some frequency of occurrence that provides antibacterial or antifungal effects. The present invention relates to ester, urethane, urea, amides, imides, carbonates, ethers, siloxanes, and many other types of linkages essential to MWF bases.

Figure 2:
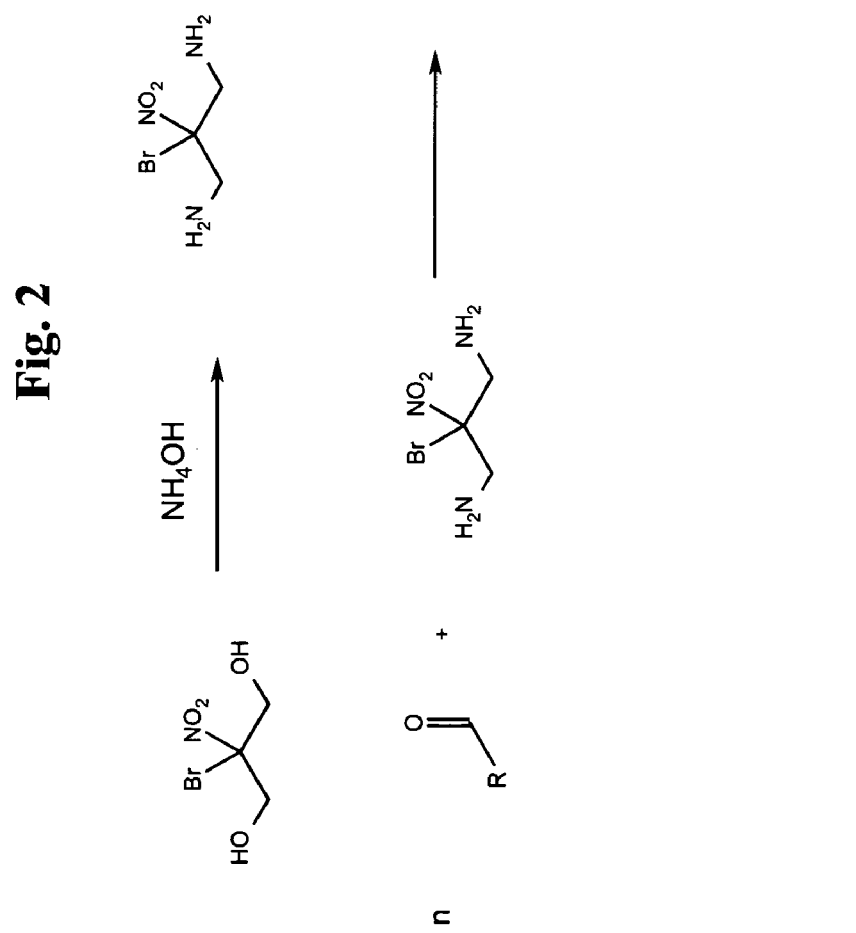
FIG. 2 shows treatment of BNPD with ammonium hydroxide to form an amide.
Figure 3:
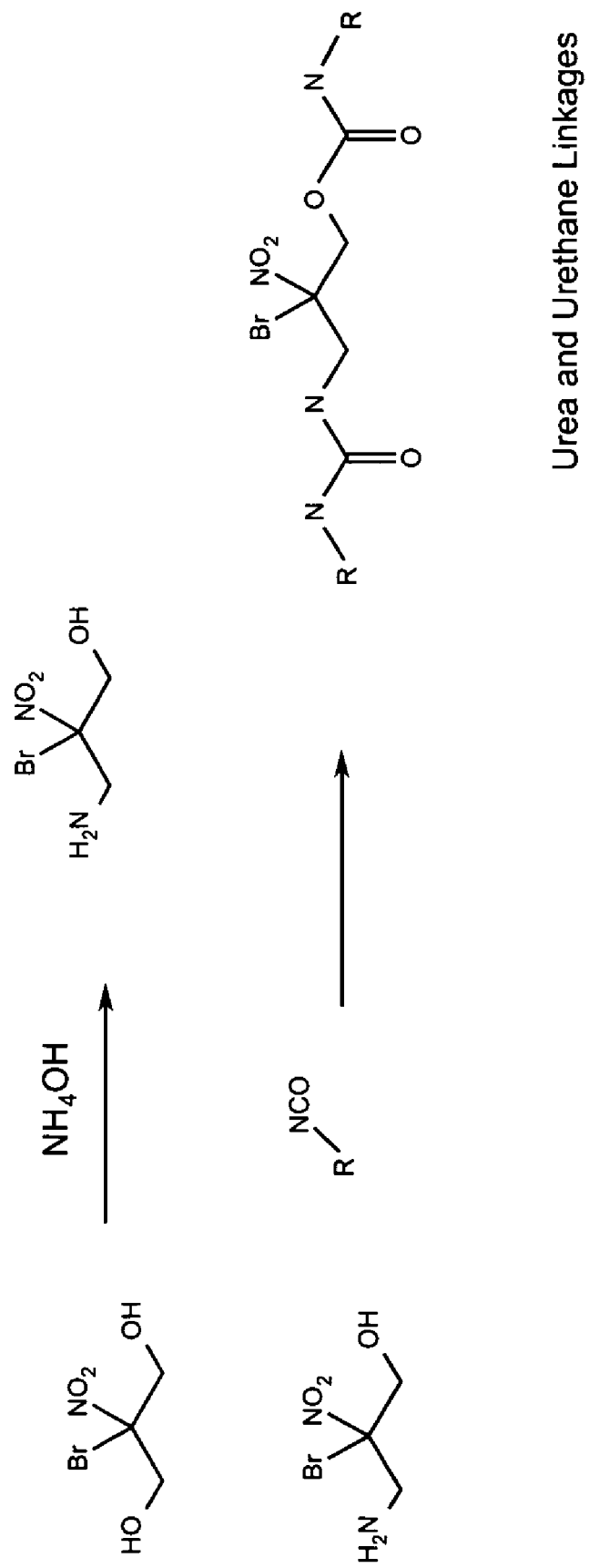
FIG. 3 shows the formation of both urethane and urea linkages.
Figure 4:
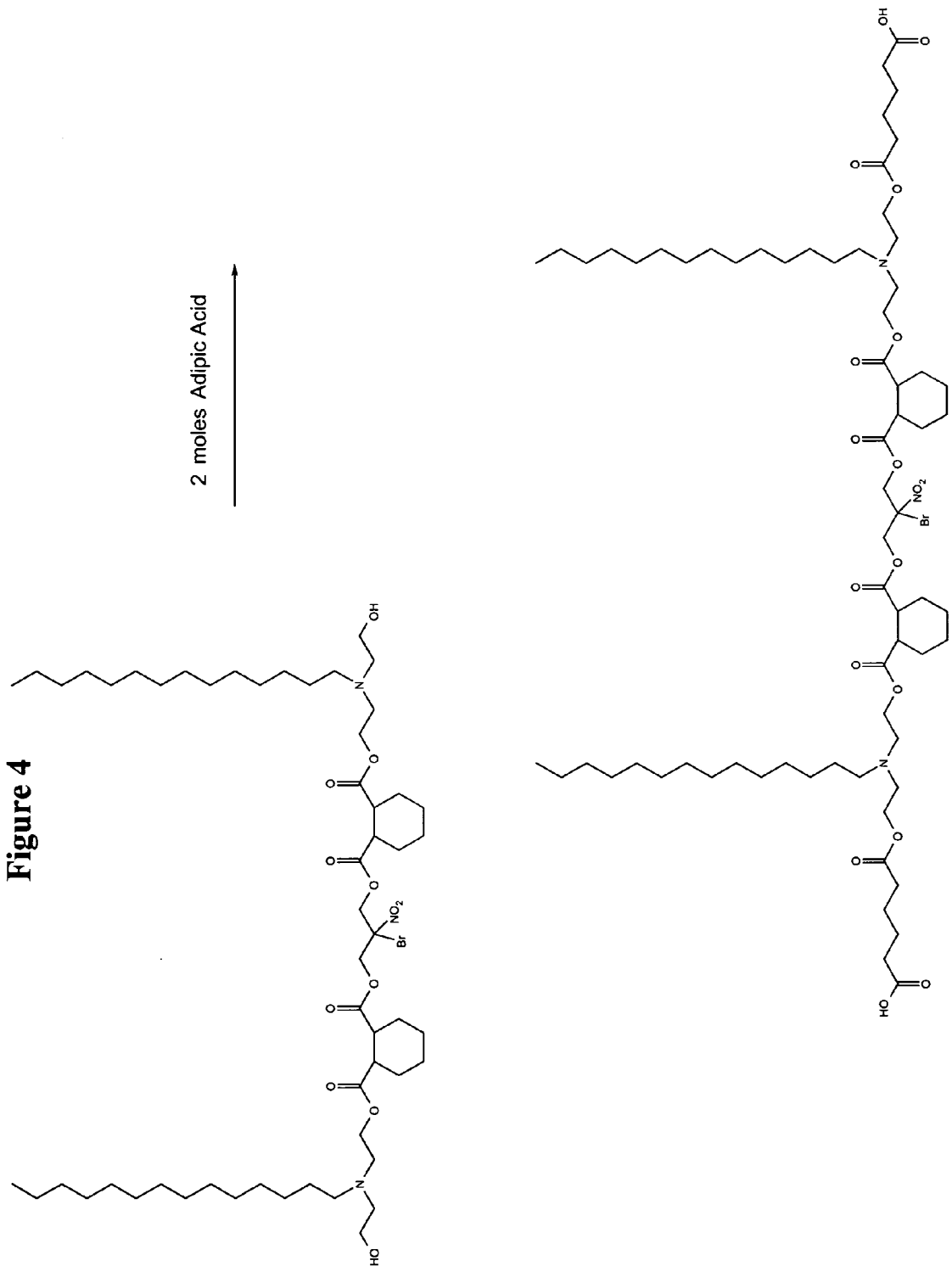
FIG. 4 shows the synthesis of an acid functional, pendant fatty chain.

FIG. 1 shows the formation of an ester linkage with BNPD. FIG. 2 shows treatment of BNPD with ammonium hydroxide to form a bromonitro amine or diamine which can then be combined with an aldehyde or carboxylic acid to form an amide. FIG. 3 shows the formation of both urethane and urea linkages. FIG. 4 shows the synthesis of an acid functional, pendant fatty chain.

The examples and illustrations presented herein are for the purpose of understanding the concepts of the present invention. It will be clear to one with ordinary skill in the art that many other examples and structures are within the scope of the present invention. This applies particularly to classes of linkages where an example of one particular structure has been given; it will be appreciated by one skilled in the art that in such a case, the entire class of compound is within the scope of the present invention.

The present invention also finds utility in coatings applications, both as monomers and additives. As a monomer or resin component, the invention will add a non-leaching antimicrobial property that is very beneficial to extend the shelf life and the life of the applied coating. This benefit is not only restricted to coatings, but to plastics and all other polymeric systems where the invention may be used as an additive or as a monomer. Medical devices such as contact lenses and catheters or other devices where a non-leaching antimicrobial is desired.

Further utility is seen when incorporated into a coatings, plastics or all other polymeric systems, either as an additive, or as a monomer that cross-links in or otherwise becomes part of the resin matrix by acting as a very powerful pigment or mineral dispersant. In addition to the effects of dispersion, increased adhesion is also achieved. The present invention produces a zero VOC system when used in combination with VOS exempt solvents. The improved adhesion and dispersant properties are not limited only to the bromo-nitro esters. The utility is also seen when the nitro ester is not halogenated, however, better results are seen with use of additional electron withdrawing groups, such as halogens, —CN, and —SO$_3$H in conjunction with the nitro group. However, good results are seen when alkyl, allyl, or an alkynal group is bound to the same carbon as the nitro moiety. This same structure also acts to improve lubricity in metal working fluids when compared to the non-nitro containing esters. While the present invention is directed primarily to esters, the moiety taught should also be effective when linked onto a carbon atom in the backbone of any suitable dispersant or adhesion promoting molecule. Dispersants and adhesion promoters within the scope of the invention include, but are not limited to urethanes, ureas, amides, esters, carbonates, ethers, acrylates, and siloxanes.

Another area where the present invention is expected to find utility is as a medical therapy against a class of illnesses caused by mycobacteria. The greater than 70 species of mycobacteria include *Mycobacterium tuberculosis*, which is responsible for tuberculosis and *Mycobacterium leprae*, which is responsible for leprosy. Other mycobacteria are responsible for opportunistic infections, especially in people with AIDS.

Mycobacteria are characterized by a content of up 60% mycolic acid in the cell wall. Mycolic acid is a waxy lipid that contributes to the impermeability of the cell wall. Mycolic acid has an average molecular weight of 1,298.4, but is not a single molecular species. The term mycolic acid (eumycolic acids) is used to describe a mixture of closely related long (60–90 carbon atoms), branch chained fatty acids with a molecular weight range of 1,108–1,307.

The waxy, impermeable cell wall impedes the entry of nutrients causing mycobacteria to grow slowly, but the low permeability also contributes to the organism's high resistance to chemical agents and resistance to lysosomal digestion by phagocytes. The BNPD esters, such as BNPD dioleate, are highly oil soluble and have similar molecular weights to mycolic acid, when considered together, BNPD esters are expected to enable the molecule to penetrate the cell wall of the mycobacteria. Once the BNPD ester permeates the cell, the bromo-nitro moiety can act upon the cell to cause cellular death, in the same way that the BNPD diesters are effective against other bacteria.

The BNPD esters of higher molecular weight are expected to show the highest levels of efficacy against mycobacteria. It is expected that the present invention will find utility as the basis of a therapy to treat these diseases, either alone, or in combination with established therapies. The preferred embodiments are expected to be BNPD dilaurate and BNPD dioleate.

I claim:

1. A pigment dispersant of the formula:

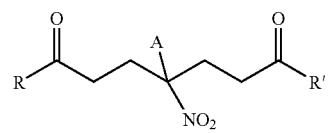

where R and R' are the same or different and are independently chosen from the group containing, linear or branched, saturated or unsaturated, alkyl, alkenyl, alkynal with from 10 to 22 carbons where A may be any halogen, —CN, —SO$_3$H, or other electron withdrawing group, or is chosen from the group containing, linear or branched, saturated or unsaturated, alkyl, alkenyl, alkynal with from 10 to 22 carbons, and wherein R or R' forms an oleate.

2. The pigment dispersant of claim 1 wherein A is bromine.

3. A pigment dispersant of the formula:
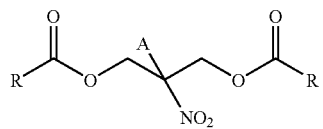
where R is —(CH$_2$)$_7$HC=CH(CH$_2$)$_7$CH$_3$ and where A may be any halogen, —CN, —SO$_3$H, or other electron withdrawing group, or is chosen from the group containing, linear or branched, saturated or unsaturated, alkyl, alkenyl, alkynal with from 10 to 22 carbons.
4. The pigment dispersant of claim 3 wherein A is bromine.
* * * * *